US012766152B2

(12) United States Patent
Seong

(10) Patent No.: US 12,766,152 B2
(45) Date of Patent: Oct. 20, 2026

(54) GEL COMPOSITION FOR PREVENTION OR TREATMENT OF ATOPIC DERMATITIS

(71) Applicant: SHAPERON INC., Seoul (KR)

(72) Inventor: Seung Yong Seong, Seoul (KR)

(73) Assignee: SHAPERON INC., Seoul (KR)

( * ) Notice: Subject to any disclaimer, the term of this patent is extended or adjusted under 35 U.S.C. 154(b) by 232 days.

(21) Appl. No.: 18/692,366

(22) PCT Filed: Sep. 15, 2022

(86) PCT No.: PCT/KR2022/013781

§ 371 (c)(1),
(2) Date: Mar. 15, 2024

(87) PCT Pub. No.: WO2023/043219

PCT Pub. Date: Mar. 23, 2023

(65) Prior Publication Data

US 2025/0134909 A1 May 1, 2025

(30) Foreign Application Priority Data

Sep. 15, 2021 (KR) ........................ 10-2021-0122994

(51) Int. Cl.

| | |
|---|---|
| ***A61K 31/575*** | (2006.01) |
| ***A61K 9/06*** | (2006.01) |
| ***A61K 47/34*** | (2017.01) |
| ***A61K 47/36*** | (2006.01) |
| ***A61P 17/00*** | (2006.01) |

(52) U.S. Cl.
CPC .............. *A61K 31/575* (2013.01); *A61K 9/06* (2013.01); *A61K 47/34* (2013.01); *A61K 47/36* (2013.01); *A61P 17/00* (2018.01)

(58) Field of Classification Search
CPC ...... A61K 31/575; A61K 47/34; A61K 47/36; A61P 17/00
See application file for complete search history.

(56) References Cited

U.S. PATENT DOCUMENTS

| | | | |
|---|---|---|---|
| 6,258,830 | B1 | 7/2001 | Charu |
| 2008/0306137 | A1 | 12/2008 | Hao |
| 2017/0196895 | A1 | 7/2017 | Seong et al. |
| 2018/0318313 | A1 | 11/2018 | Sengupta et al. |

FOREIGN PATENT DOCUMENTS

| | | | |
|---|---|---|---|
| KR | 20170013854 | A | 2/2017 |
| WO | 2004073614 | A2 | 9/2004 |
| WO | 2020186010 | A1 | 9/2020 |

OTHER PUBLICATIONS

International Search Report dated Dec. 26, 2022 for corresponding International Application No. PCT/KR2022/013781, 13 pages (with English language translation).
Silva et al., "Clobetasol-loaded nanostructured lipid carriers for epidermal targeting", Journal of Pharmacy and Pharmacology, vol. 68, 2016, pp. 742-750.

*Primary Examiner* — Bruck Kifle
(74) *Attorney, Agent, or Firm* — MH2 Technology Law Group, LLP

(57) ABSTRACT

The present invention relates to a gel composition comprising taurodeoxycholic acid, its derivative, or a pharmaceutically acceptable salt thereof as an active ingredient, hyaluronic acid, its derivative, or a pharmaceutically acceptable salt thereof; and a surfactant that is polysorbate 20 or polysorbate 80, and a composition comprising the same for preventing or treating atopic dermatitis, and specifically, the composition has fewer side effects and higher therapeutic efficacy compared to existing atopic dermatitis treatments, it is effective and has a significantly superior effect compared to conventional formulations, and so it can be usefully used as a new pharmaceutical composition that can prevent or treat atopic dermatitis.

20 Claims, 14 Drawing Sheets

【Figure 1】
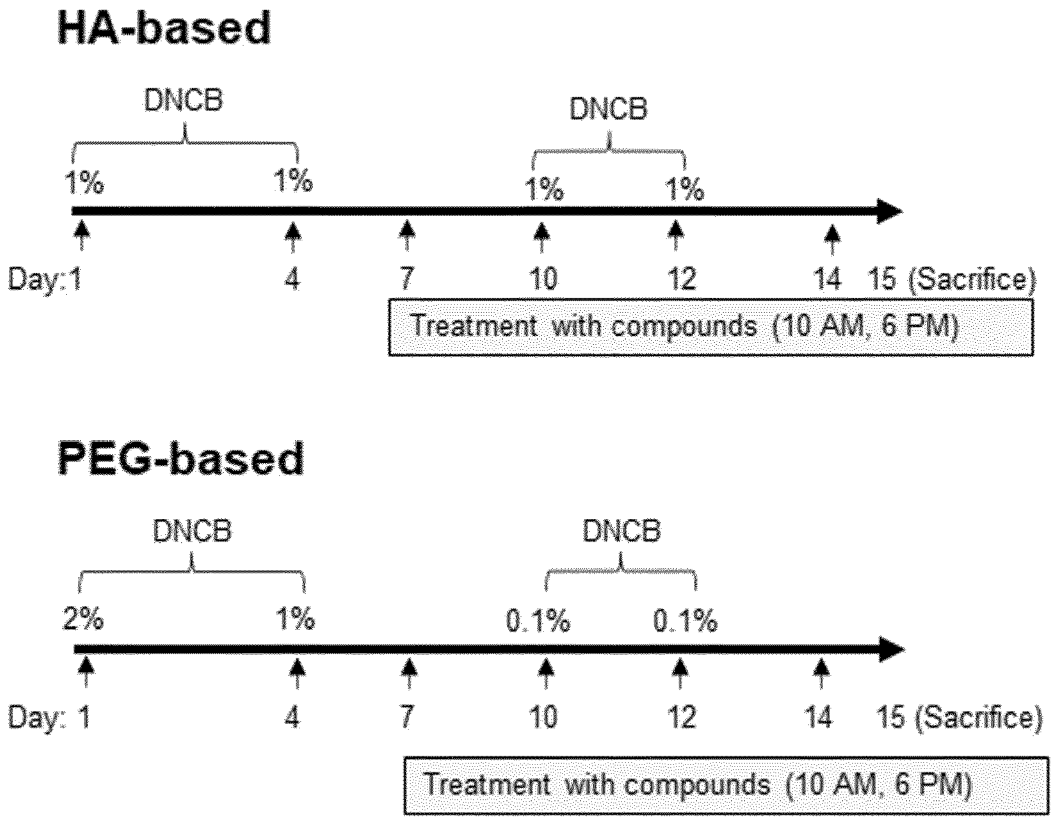

【Figure 2】
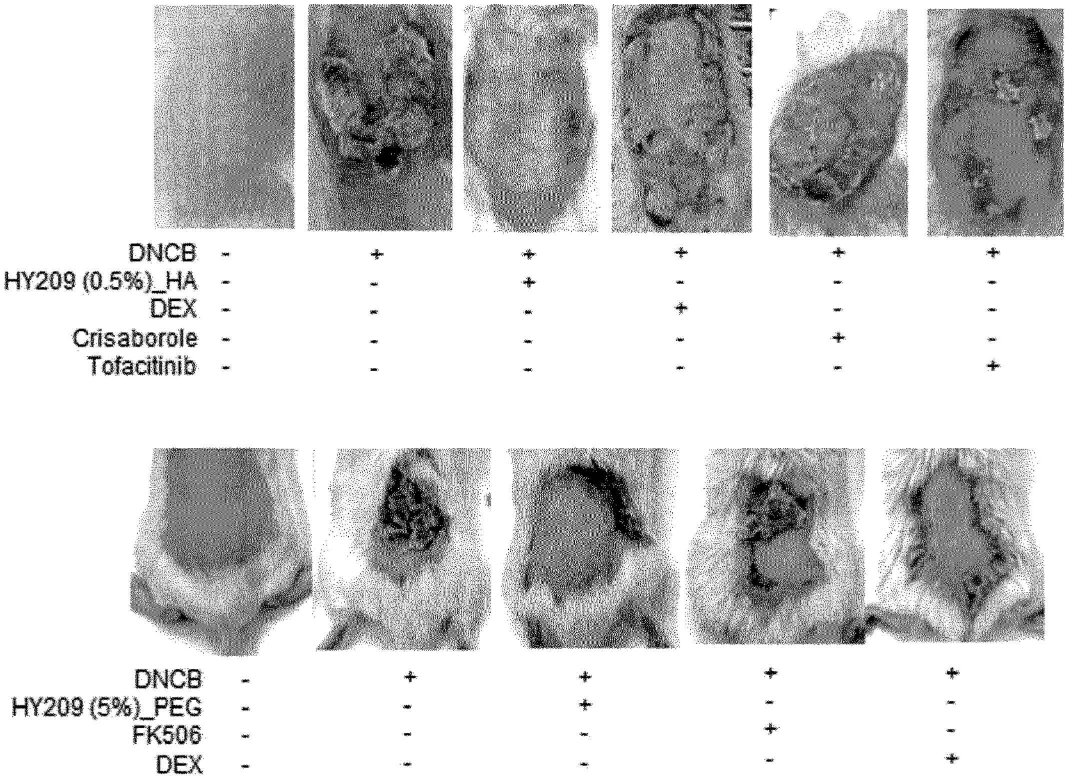

【Figure 3】
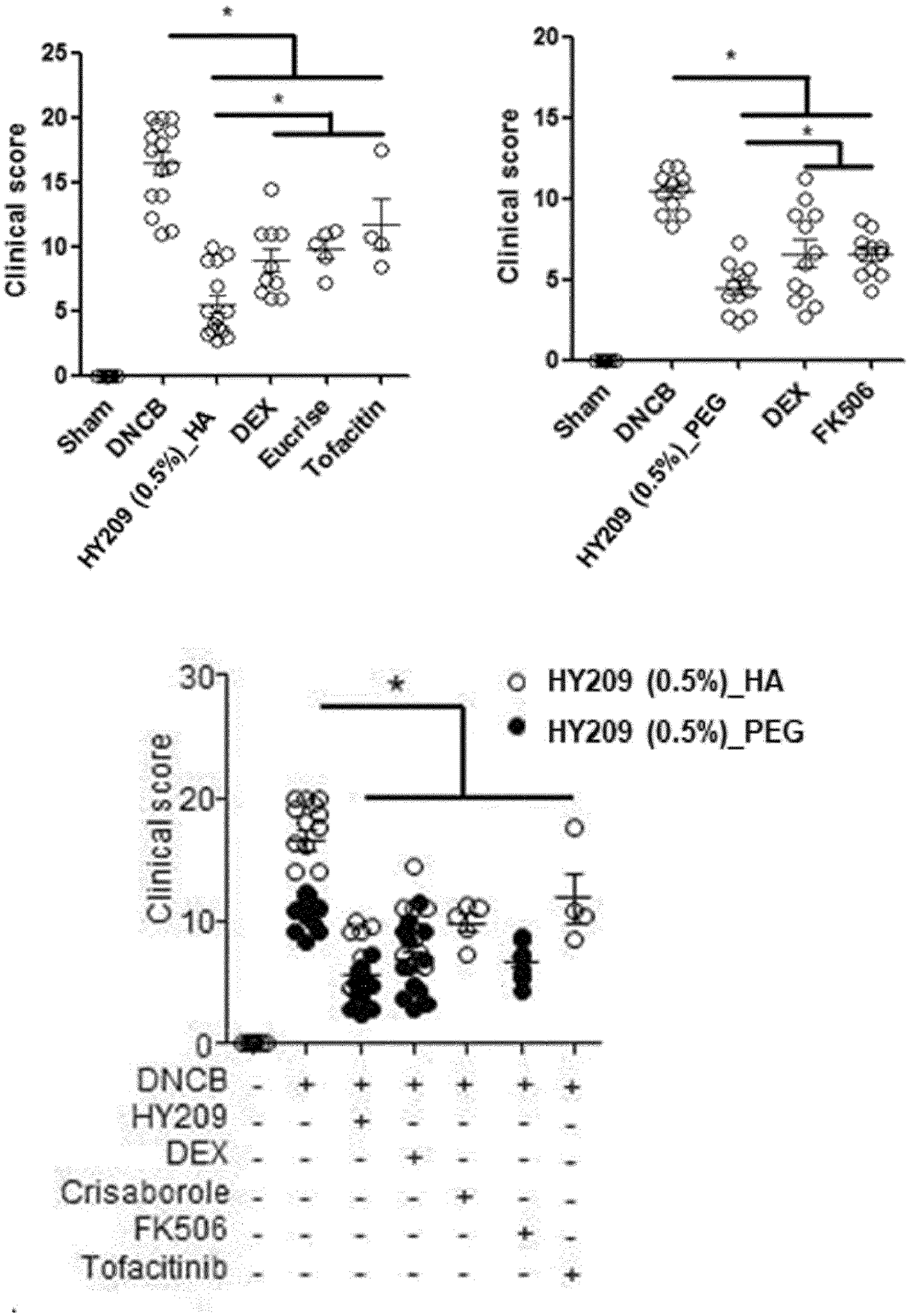

【Figure 4】
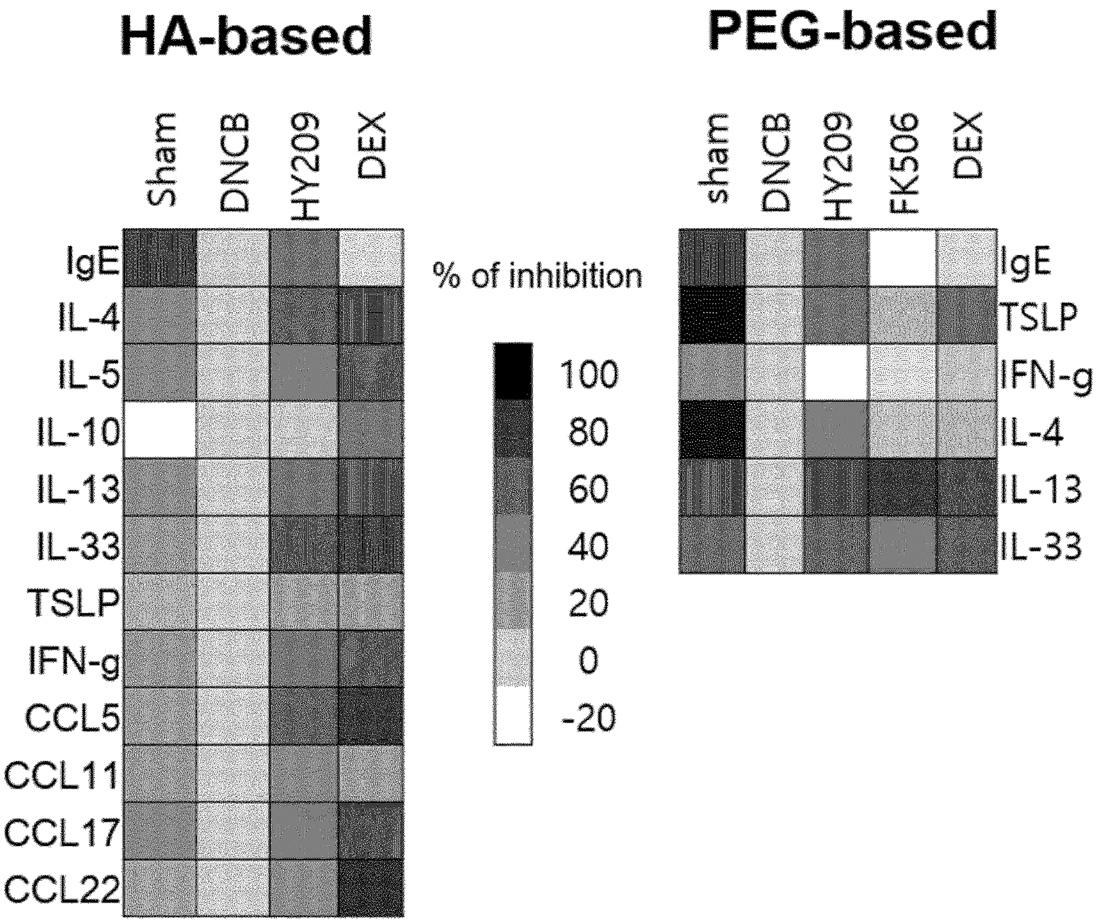

【Figure 5】
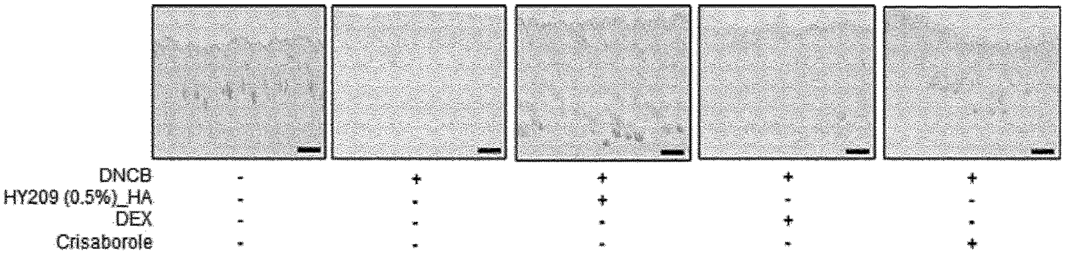
| | | | | | |
|---|---|---|---|---|---|
| DNCB | - | + | + | + | + |
| HY209 (0.5%)_HA | - | - | + | - | - |
| DEX | - | - | - | + | - |
| Crisaborole | - | - | - | - | + |
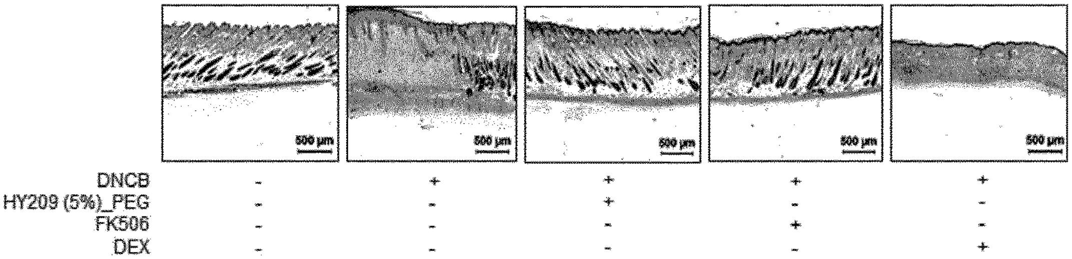
| | | | | | |
|---|---|---|---|---|---|
| DNCB | - | + | + | + | + |
| HY209 (5%)_PEG | - | - | + | - | - |
| FK506 | - | - | - | + | - |
| DEX | - | - | - | - | + |

【Figure 6】
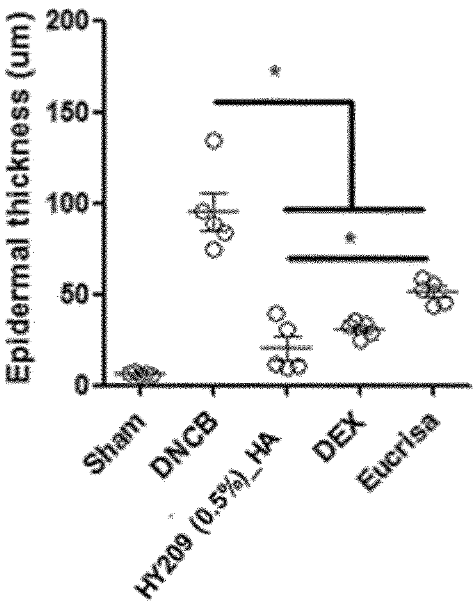
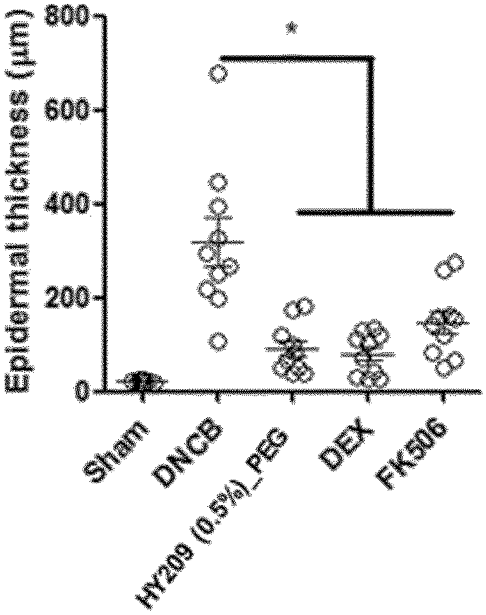
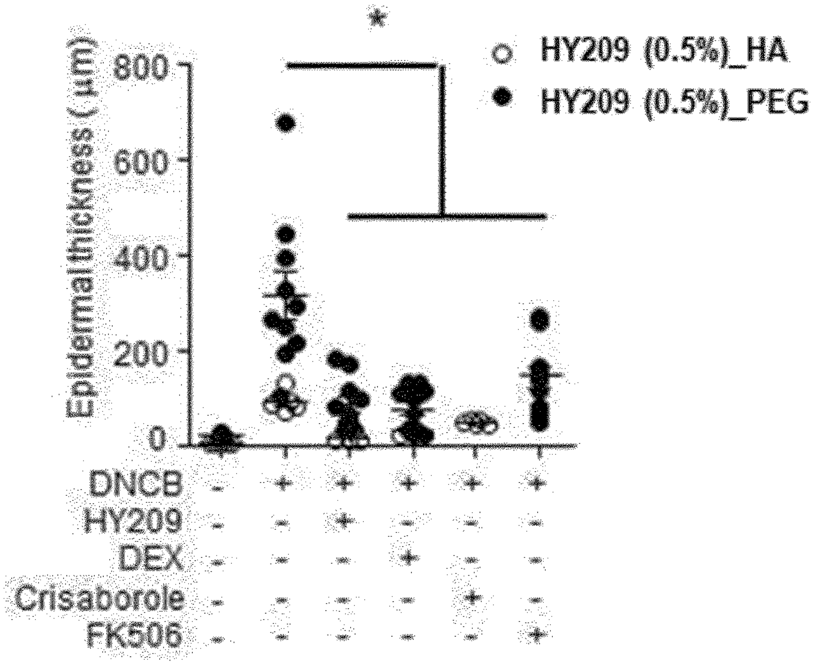

【Figure 7】
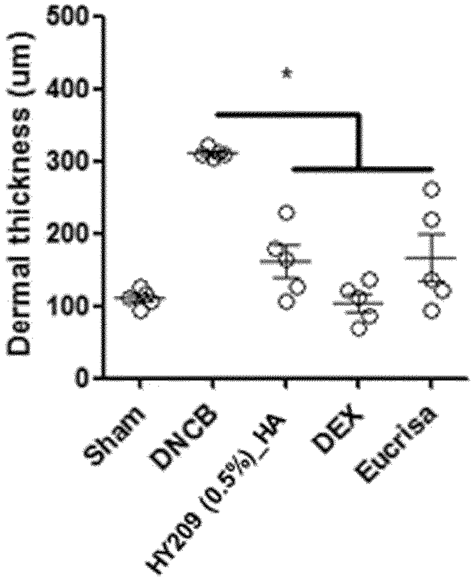
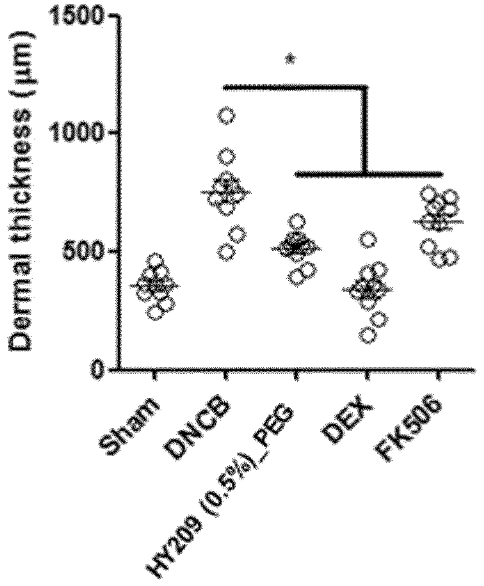
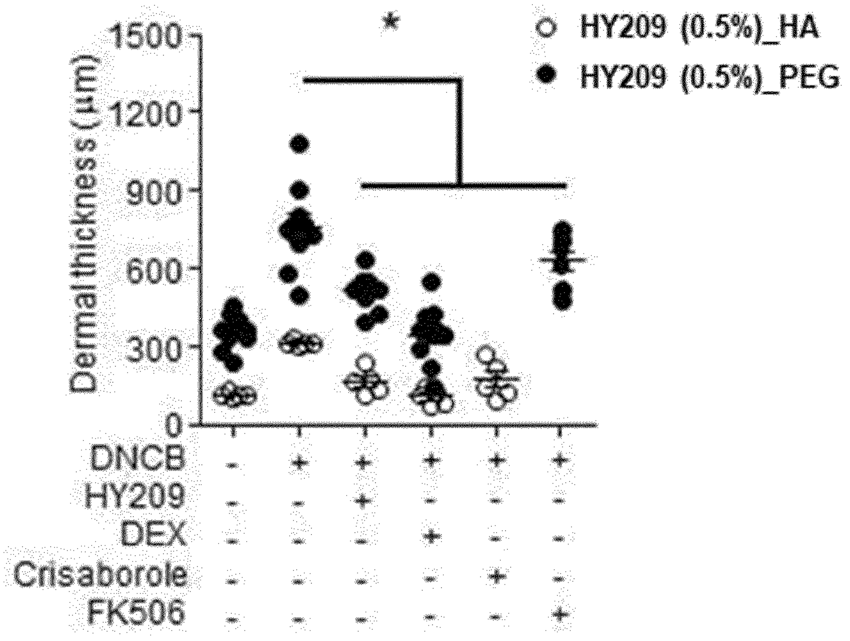

【Figure 8】
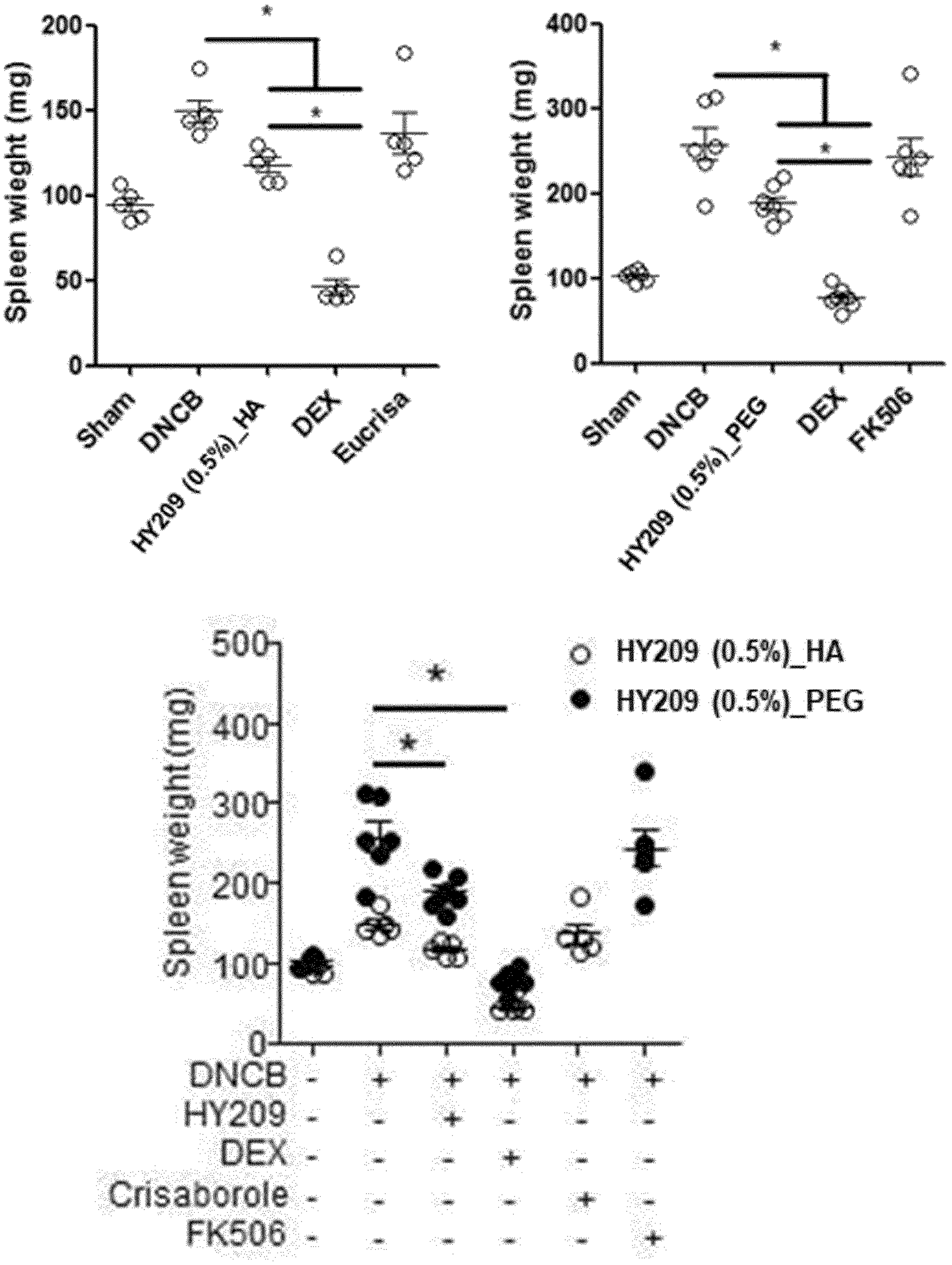

【Figure 9】
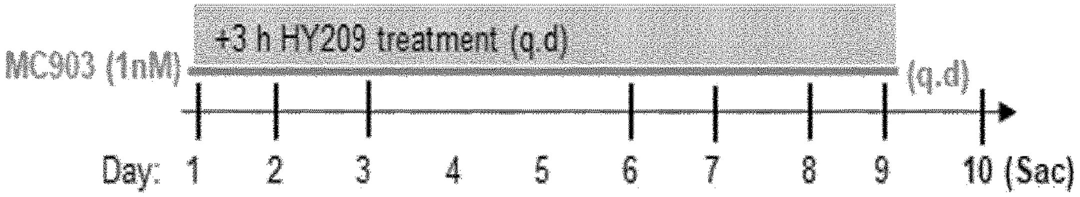

【Figure 10】
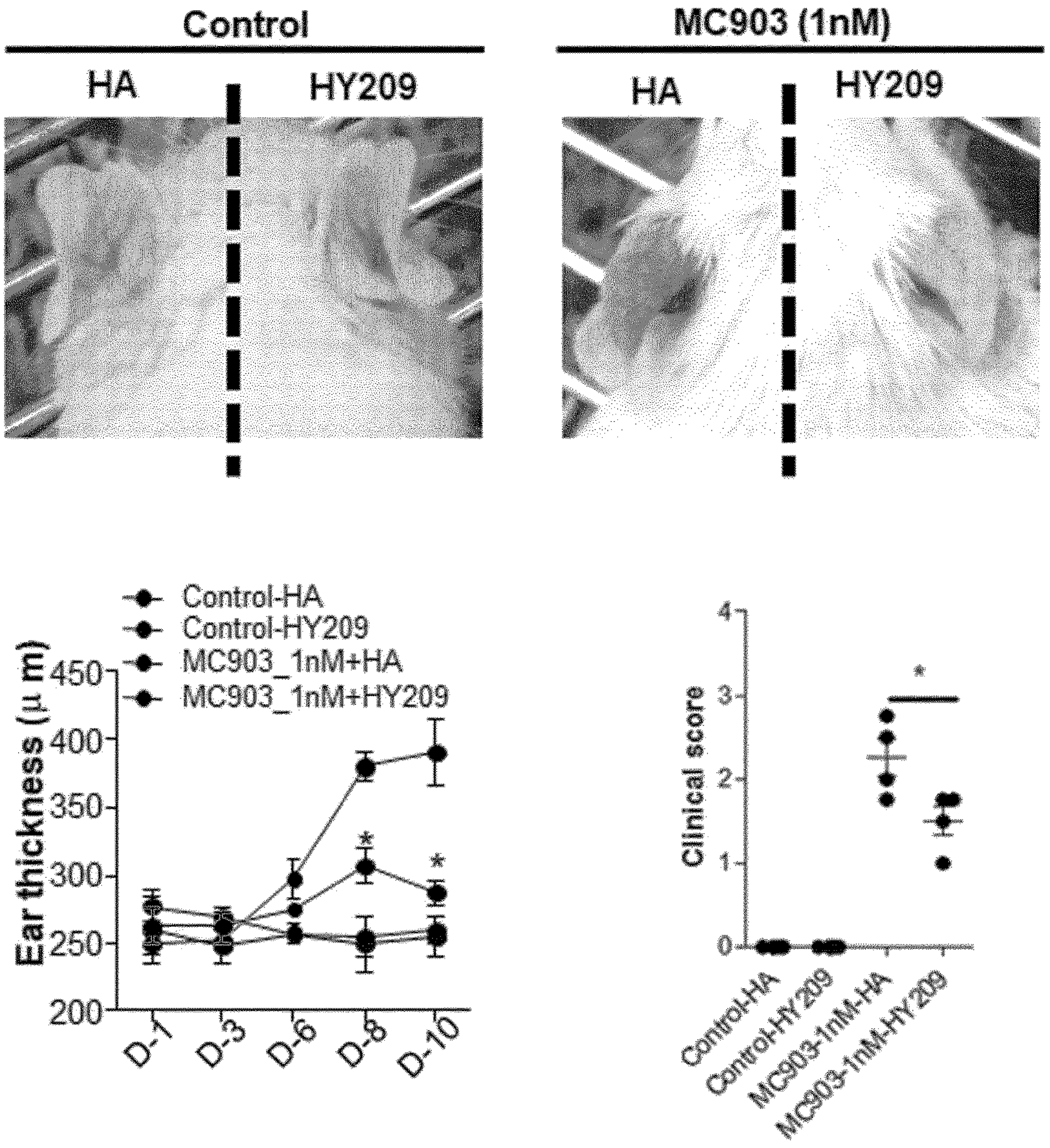

【Figure 11】
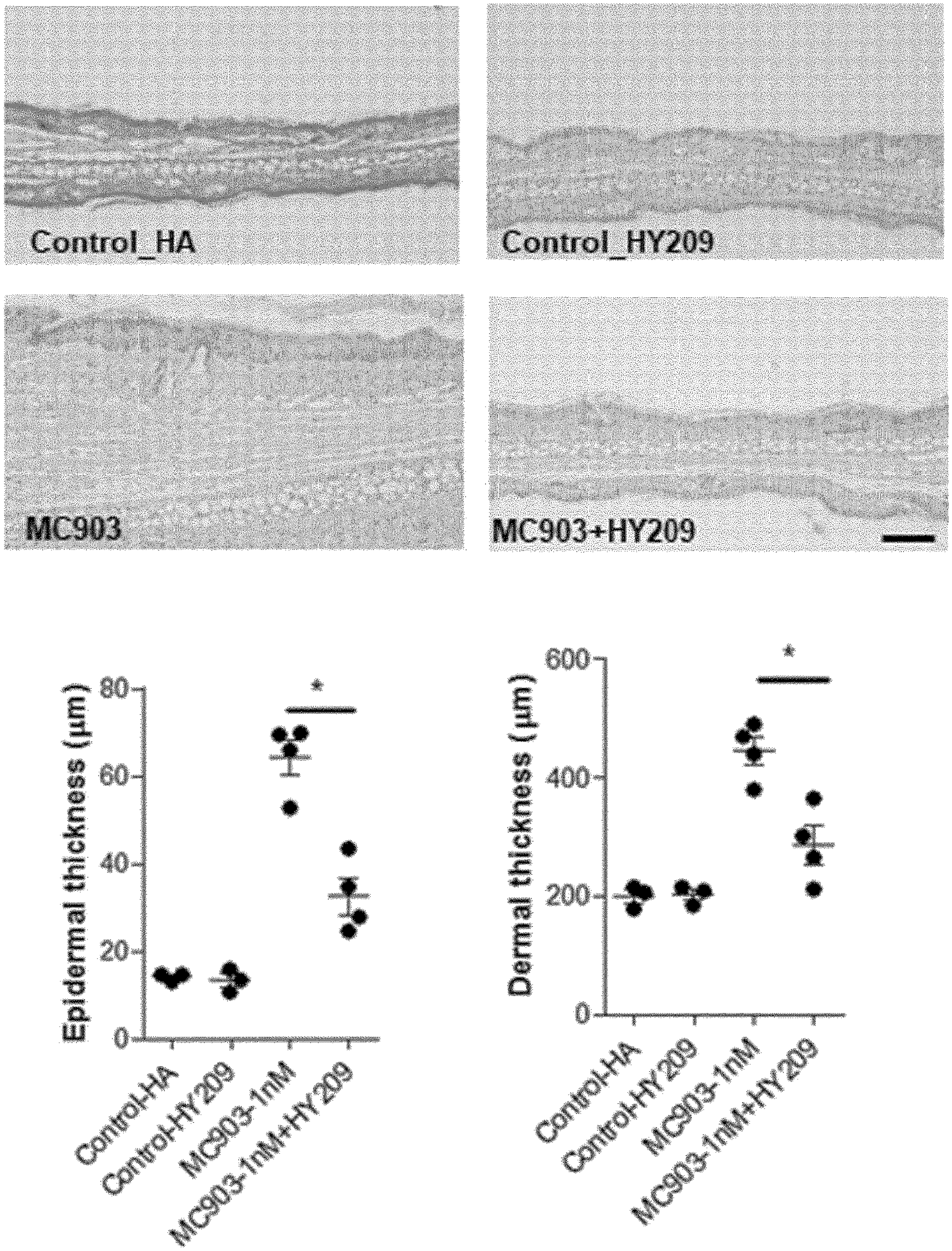

【Figure 12】
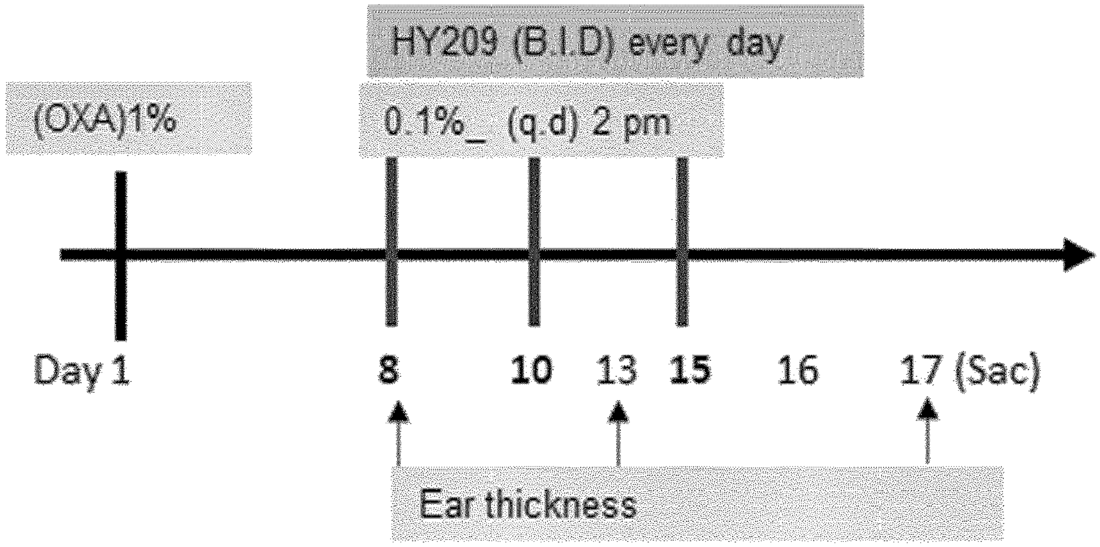

【Figure 13】
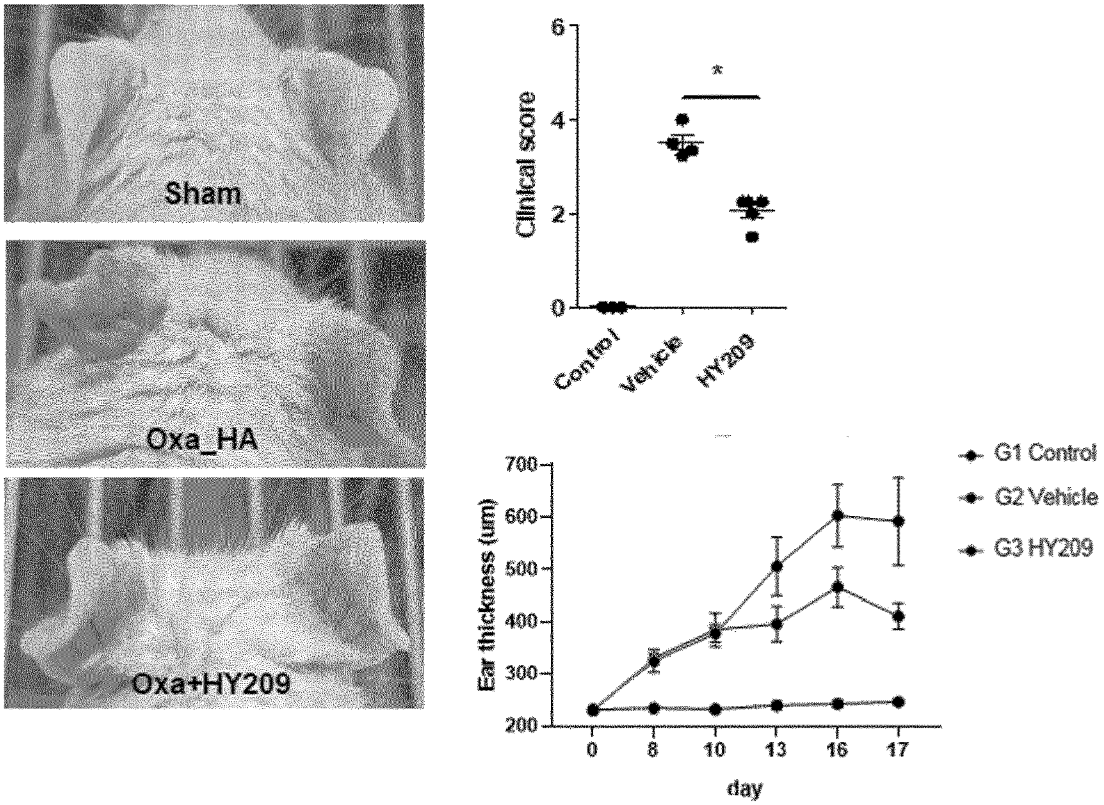

【Figure 14】
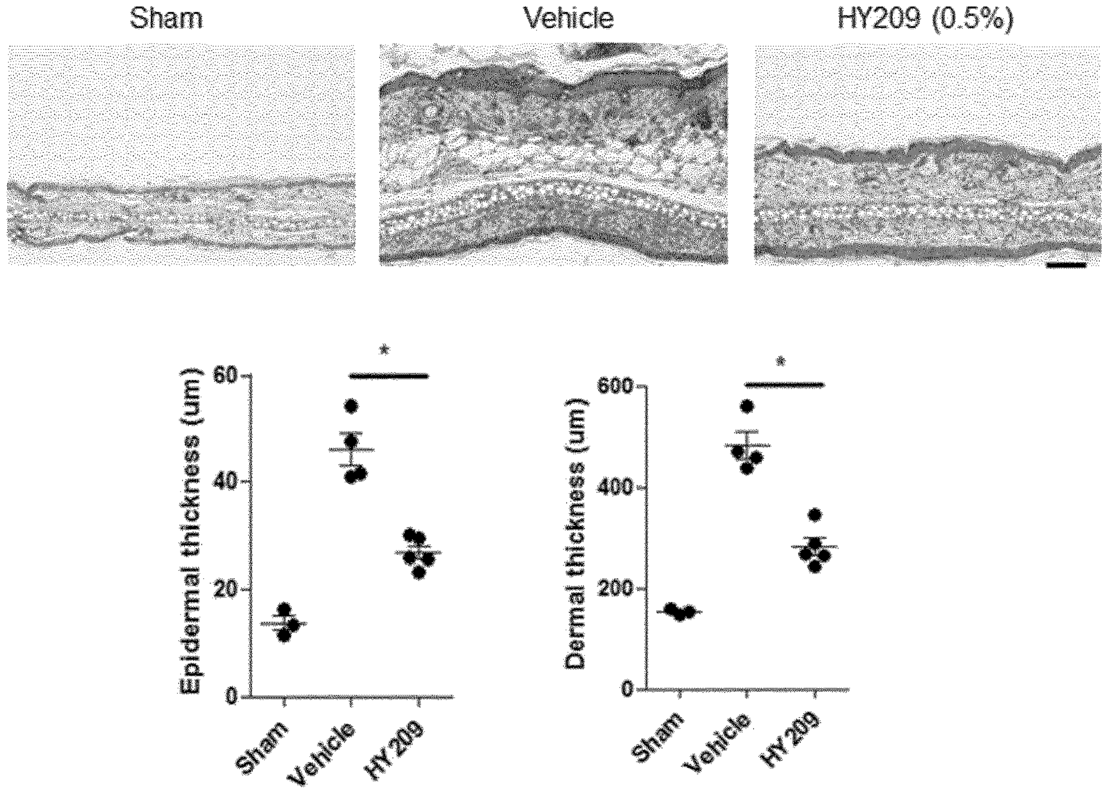

GEL COMPOSITION FOR PREVENTION OR TREATMENT OF ATOPIC DERMATITIS

CROSS-REFERENCE TO RELATED APPLICATIONS

This application is a U.S. national stage application of PCT/KR2022/013781 filed 15 Sep. 2022, which claims the benefit of, and relies on the filing date of, Korean Patent Application No. 10-2021-0122994 filed 15 Sep. 2021, the entire disclosure of which is incorporated herein by reference.

FIELD OF THE INVENTION

The present invention relates to a gel composition comprising taurodeoxycholic acid, its derivative, or a pharmaceutically acceptable salt thereof as an active ingredient, and hyaluronic acid, its derivative, or a pharmaceutically acceptable salt thereof; and a surfactant such as polysorbate 20 or polysorbate 80, its use in preventing, treating or improving atopic dermatitis, and a method for producing the same.

BACKGROUND OF THE INVENTION

The tendency to develop dermatitis, asthma, and hay fever due to substances exposed to food and the respiratory tract was first described by Coca in 1925 as atopy. In addition to atopic dermatitis, atopic diseases include asthma, allergic rhinitis, and allergic conjunctivitis. The incidence of atopic dermatitis is rapidly increasing worldwide due to the increase in environmental pollutants and the like, and the prevalence reaches 20% of the total population. Atopic dermatitis patients' quality of life is declining due to limitations in their daily lives, and the economic burden of treatment is increasing on society. Therefore, atopy treatment management measures are urgently needed. Atopic dermatitis is a recurrent chronic skin disease accompanied by severe itching that usually begins in infancy or childhood and is a very common skin disease with a family history. Symptoms begin in infants and toddlers, especially around 2 months of age, approximately 50% of cases occur before 2 years of age, and most symptoms appear before 5 years of age, however, it is very rare for symptoms to first appear in adults. For some patients, symptoms are alleviated or healed naturally as they grow, and more than half of patients who develop it in infancy improve before the age of two. The shape and distribution of skin lesions are characteristic and are accompanied pruritus (itching), dry skin, and characteristic eczema. In infancy, it begins as eczema on the face and outstretched sides of the limbs, but as it grows, it characteristically appears in the areas where the arms bend and behind the knees. In adults, lichenification, a thickening of the skin in the folds, occurs, and compared to children, eczema often occurs on areas other than the extremities, such as the face, chest, and nape of the neck.

The tendency to develop dermatitis, asthma, and hay fever due to substances exposed to food and the respiratory tract was first described by Coca in 1925 as atopy. In addition to atopic dermatitis, atopic diseases include asthma, allergic rhinitis, and allergic conjunctivitis. The incidence of atopic dermatitis is rapidly increasing worldwide due to the increase in environmental pollutants, and the prevalence reaches 20% of the total population. Atopic dermatitis patients' quality of life is declining due to limitations in their daily lives, and the economic burden of treatment is increasing on society. Therefore, atopy treatment management measures are urgently needed. Atopic dermatitis is a recurrent chronic skin disease accompanied by severe itching that usually begins in infancy or childhood and is a very common skin disease with a family history. Symptoms begin in infants and toddlers, especially around 2 months of age. Approximately 50% of cases occur before 2 years of age, and most symptoms appear before 5 years of age. However, it is very rare for symptoms to first appear in adults. For some patients, symptoms are alleviated or healed naturally as they grow, and more than half of patients who develop it in infancy improve before the age of two. The shape and distribution of skin lesions are characteristic and are accompanied by pruritus (itching), dry skin, and characteristic eczema. In infancy, it begins as eczema on the face and outstretched sides of the limbs, but as it grows, it characteristically appears in the areas where the arms bend and behind the knees. In adults, lichenification, a thickening of the skin in the folds, occurs, and compared to children, eczema often occurs on areas other than the extremities, such as the face, chest, and nape of the neck.

Atopy is usually accompanied by an allergic reaction. In particular, atopic dermatitis is not only a skin disease, but also a sign of an allergic march such as allergic asthma and rhinitis. However, the exact cause and mechanism of atopic dermatitis have not yet been identified, so a suitable treatment that can completely cure it has not been developed. Currently, antihistamines, steroids, and immunomodulators are used as treatments for atopic dermatitis. Anti-inflammatory analgesics and steroid-based immunosuppressants are mainly used to relieve inflammation and immune response, and they have the advantage of showing rapid improvement, but symptoms can rapidly worsen if the medication is reduced or discontinued, and long-term use can cause systemic side effects such as secondary adrenocortical insufficiency, diabetes, peptic ulcers, hirsutism, alopecia, and pigmentation may occur, and it may cause cataracts, especially in children. Steroid ointments cause serious side effects such as thinning or atrophy of the skin, redness and folliculitis due to enlarged blood vessels. Elidel (pimecrolimus) cream and Protopic (tacrolimus, FK506) ointments, which are non-steroidal immunomodulators, have been developed as medicines that can replace steroid ointments, so they do not have the side effects that occur with existing steroid ointments when applied for a long period of time, so they can be used on the face or skin, and tt is often used on sensitive skin such as the neck, and has grown rapidly to 30% of the total atopic dermatitis market. However, recently, the risk of calcineurin inhibitors' potential to cause cancer has been raised, and their use is only permitted in low concentrations in patients under 16 years of age, and use in low concentrations is not permitted in children under 2 years of age, so sales are decreasing. In the treatment of other atopic dermatitis, antihistamines and, in severe cases, short-term administration of corticosteroids and application of topical agents, and treatment with ultraviolet rays of the skin or interferon treatment are performed, however, in most cases, it is an incurable disease that shows temporary improvement but relapses when the medication is stopped. Therefore, there is an urgent need to develop therapeutic and preventive drugs that have fewer side effects and are more effective than existing treatments.

Therefore, the present inventors confirmed that a gel composition comprising taurodeoxycholic acid, its derivative, or a pharmaceutically acceptable salt thereof as an active ingredient, along with hyaluronic acid, its derivative, or a pharmaceutically acceptable salt thereof, and a surfactant such as polysorbate 20 or polysorbate 80, exhibits a significant effect in atopic treating dermatitis, furthermore, it demonstrates a significantly superior effect compared to existing formulations, and as a result, the present invention was completed by revealing its potential for use in preventing, treating, or improving atopic dermatitis.

DETAILED DESCRIPTION OF THE INVENTION

Technical Challenges

The object of the present invention is to provide a gel composition comprising taurodeoxycholic acid, its derivative, or a pharmaceutically acceptable salt thereof as an active ingredient, along with hyaluronic acid, its derivative, or a pharmaceutically acceptable salt thereof, and a surfactant selected from polysorbate 20 or polysorbate 80, and an agent for prevention or treatment of atopic dermatitis comprising the same.

In addition, another object of the present invention is to provide a method for preventing, improving, or treating atopic dermatitis, comprising administering the gel composition to a subject.

In addition, another object of the present invention is to provide the use of the gel composition for use as a pharmaceutical composition for preventing or treating atopic dermatitis.

In addition, another object of the present invention is to provide a use of the gel composition for use as a cosmetic composition for preventing or improving atopic dermatitis.

Technical Solutions

In order to achieve the above object, the present invention provides, a gel composition comprising taurodeoxycholic acid, its derivative, or a pharmaceutically acceptable salt thereof as an active ingredient; hyaluronic acid, its derivative, or a pharmaceutically acceptable salt thereof; and a surfactant that is polysorbate 20 or polysorbate 80.

Additionally, the gel composition can be used as a composition for preventing or treating atopic dermatitis.

Additionally, the gel composition can be used as a cosmetic composition for preventing or improving atopic dermatitis.

Additionally, the present invention provides a method for preventing or improving atopic dermatitis, comprising administering the gel composition to a subject.

Additionally, the present invention provides a method of treating atopic dermatitis, comprising administering the gel composition to a subject.

Additionally, the present invention provides the use of the gel composition for use as a pharmaceutical composition for preventing or treating atopic dermatitis.

In addition, the present invention provides the use of the gel composition for use as a cosmetic composition for preventing or improving atopic dermatitis.

Technical Effect

The gel composition according to the present invention has fewer side effects and has a higher therapeutic effect than existing atopic dermatitis treatments, and it has also been confirmed that it exhibits a significant effect compared to conventional formulations, so it can be usefully used as a composition for preventing, treating or improving atopic dermatitis.

BRIEF DESCRIPTION OF THE DRAWINGS

FIG. 1 is a diagram showing the injection time of DNCB for inducing atopic dermatitis in mice and the injection time of 0.5% HY209_HA gel and 5% HY209_PEG gel for treating atopic dermatitis.

FIG. 2 is a diagram showing the atopic dermatitis-induced area in mice treated with various therapeutic agents including 0.5% HY209_HA gel and 5% HY209_PEG gel after inducing atopic dermatitis with DNCB.

FIG. 3 is a graph showing the results of sensory evaluation of mice treated with various therapeutic agents including 0.5% HY209_HA gel and 5% HY209_PEG gel after inducing atopic dermatitis with DNCB.

FIG. 4 is a graph showing the various cytokine inhibition abilities of mice treated with various therapeutic agents including 0.5% HY209_HA gel and 5% HY209_PEG gel after inducing atopic dermatitis with DNCB.

FIG. 5 is a diagram showing a comparison of the epithelium and dermis of mice treated with various therapeutic agents including 0.5% HY209_HA gel and 5% HY209_PEG gel after inducing atopic dermatitis with DNCB.

FIG. 6 is a graph showing the results of epithelial thickness measurements in mice treated with various therapeutic agents including 0.5% HY209_HA gel and 5% HY209_PEG gel after inducing atopic dermatitis with DNCB.

FIG. 7 is a graph showing the dermal thickness measurement results of mice treated with various therapeutic agents including 0.5% HY209_HA gel and 5% HY209_PEG gel after inducing atopic dermatitis with DNCB.

FIG. 8 is a graph showing the results of measuring spleen weight in mice treated with various therapeutic agents including 0.5% HY209_HA gel and 5% HY209_PEG gel after inducing atopic dermatitis with DNCB.

FIG. 9 is a diagram showing the injection time of MC903 for inducing atopic dermatitis in mice and the injection time of 0.5% HY209_HA gel for treating atopic dermatitis.

FIG. 10 is a diagram showing the atopic dermatitis-induced area in mice treated with various treatments including 0.5% HY209_HA gel after inducing atopic dermatitis with MC903, and a graph showing the sensory evaluation results and ear thickness.

FIG. 11 is a diagram comparing the epithelium and dermis of mice treated with various therapeutic agents including 0.5% HY209_HA gel after inducing atopic dermatitis with MC903, and a graph showing the results of measuring the thickness of the epidermis and dermis.

FIG. 12 is a diagram showing the injection time of oxazolone for inducing atopic dermatitis in mice and the injection time of 0.5% HY209_HA gel for treating atopic dermatitis.

FIG. 13 is a diagram showing the atopic dermatitis-induced area in mice treated with various treatments including 0.5% HY209_HA gel after inducing atopic dermatitis with oxazolone, and a graph showing the sensory evaluation results and ear thickness.

FIG. 14 is a diagram comparing the epithelium and dermis of mice treated with various therapeutic agents including 0.5% HY209_HA gel after inducing atopic dermatitis with oxazolone, and a graph showing the results of measuring the thickness of the epithelium and dermis.

DETAILED DESCRIPTION OF PREFERRED EMBODIMENTS

Hereinafter, the present invention will be described in more detail.

The present invention provides, a gel composition comprising taurodeoxycholic acid, its derivative, or a pharmaceutically acceptable salt thereof as an active ingredient;

hyaluronic acid, its derivative, or a pharmaceutically acceptable salt thereof; and a surfactant selected from polysorbate 20 or polysorbate 80.

In addition, the present invention provides, a gel composition for use as a pharmaceutical composition for the prevention or treatment of atopic dermatitis, comprising taurodeoxycholic acid, its derivative, or a pharmaceutically acceptable salt thereof as an active ingredient; hyaluronic acid, its derivative, or a pharmaceutically acceptable salt thereof; and a surfactant selected from polysorbate 20 or polysorbate 80.

In the present invention, the taurodeoxycholic acid may be sodium taurodeoxycholic acid, but is not limited thereto.

In the present invention, taurodeoxycholic acid, its derivative, or a pharmaceutically acceptable salt thereof as an active ingredient is included as an active ingredient in an amount ranging from 0.01 to 3 w/v % based on the entire gel composition; specifically it may be included at 0.01 to 1 w/v %; more specifically at 0.02 to 0.5 w/v %; and even more specifically, it may be included at 0.05 to 0.1 w/v %.

In the present invention, the hyaluronic acid, its derivative, or a pharmaceutically acceptable salt thereof may be sodium hyaluronic acid.

In the present invention, the hyaluronic acid, its derivative or a pharmaceutically acceptable salt thereof is included in an amount ranging from 0.1 to 2 w/v % based on the entire gel composition; specifically it may be included at 0.1 to 2 w/v %; 0.5 to 1.5 w/v %; more specifically, it may be included at 1 w/v %.

In the present invention, the surfactant, which is polysorbate 20 or polysorbate 80, is included in an amount ranging from 0.01 to 1 w/v % based on the entire gel composition; specifically it may be included at 0.02 to 0.5 w/v %; more specifically 0.03 to 0.1 w/v %; even more specifically, it may be included at 0.05 w/v %.

In the present invention, Polysorbate 20 can be used as a surfactant.

In the present invention, the gel composition may further include a preservative.

In the present invention, methyl paraoxybenzoate can be used as the preservative.

In the present invention, the preservative may be included in an amount ranging from 0.05 to 1 w/v % based on the entire gel composition; specifically it may be included at 0.1 to 0.5 w/v %; more specifically, it may be included at 0.2 w/v %.

In the present invention, the gel composition may further contain additives such as stabilizers, wetting agents and/or emulsifiers, solubilizers, solvents, salts and/or buffers for adjusting osmotic pressure, but is not limited thereto.

In the present invention, the gel composition may be a pharmaceutical composition for preventing or treating atopic dermatitis.

In the present invention, the gel composition may be a cosmetic composition for preventing or improving atopic dermatitis.

In the present invention, the gel composition may be a gel composition for animals for preventing, improving, or treating atopic dermatitis.

In the present invention, the dosage of the gel composition comprising taurodeoxycholic acid, its derivative, or a pharmaceutically acceptable salt thereof as an active ingredient is determined by various factors, such as the effectiveness and duration of action of the active ingredient, the method of administration, individual conditions such as sex, age, weight, and severity of other diseases in warm-blooded animals. A specific administration route and dosage may be selected by the doctor/veterinarian in charge depending on the characteristics of the subject to be administered, such as age, weight, disease state, body condition, and other relevant factors.

In the present invention, a method for preparation of a gel composition comprising:

(a) obtaining a gel formulation by blending taurodeoxycholic acid, its derivative, or a pharmaceutically acceptable salt thereof; and hyaluronic acid, its derivative, or a pharmaceutically acceptable salt thereof; and (b) adding a surfactant selected from polysorbate 20 or polysorbate 80 and stirring.

In step (a), the taurodeoxycholic acid may be sodium taurodeoxycholic acid, and taurodeoxycholic acid, its derivative, or a pharmaceutically acceptable salt thereof may be included in an amount ranging from 0.01 to 3 w/v %; specifically at 0.01 to 1 w/v %; more specifically at 0.02 to 0.5 w/v %; even more specifically, it may be included at 0.05 to 0.1 w/v % based on the entire gel composition.

In step (a), the hyaluronic acid, its derivative, or a pharmaceutically acceptable salt thereof may be sodium hyaluronic acid, and the hyaluronic acid, its derivative, or a pharmaceutically acceptable salt thereof may be included in an amount ranging from 0.1 to 2 w/v %; specifically 0.1 to 2 w/v %; 0.5 to 1.5 w/v %; more specifically, it may be included at 1 w/v % based on the entire gel composition.

In step (b), the surfactant, which is polysorbate 20 or polysorbate 80, is included in an amount ranging from 0.01 to 1 w/v % based on the entire gel composition; specifically 0.02 to 0.5 w/v %; more specifically 0.03 to 0.1 w/v %; even more specifically, it may be included at 0.05 w/v %.

In a specific example of the present invention, the inventors prepared HY209 gel containing sodium taurodeoxycholic acid and added sodium hyaluronate, and then applied the HY209 gel to mice suffering from atopic dermatitis, resulting in 0.5% HY209 gel demonstrated notable efficacy in alleviating each symptom of atopic dermatitis, and importantly, it has been confirmed that this formulation is significantly superior compared to existing treatments for atopic dermatitis, including the applicant's own products.

Therefore, the composition for preventing, treating or improving atopic dermatitis containing taurodeoxycholic acid and its derivatives as an active ingredient and hyaluronic acid and its derivatives as an excipient of the present invention is used in mice suffering from atopic dermatitis since it shows a significant effect in treating or improving atopic dermatitis in skin application experiments, the composition can be usefully used as an active ingredient in a composition for preventing, treating, or improving atopic dermatitis.

In addition, the present invention provides a method of preventing or improving atopic dermatitis comprising administering a gel composition to a subject, comprising taurodeoxycholic acid, its derivative, or a pharmaceutically acceptable salt thereof as an active ingredient;

hyaluronic acid, its derivatives or pharmaceutically acceptable salts thereof; and a surfactant selected from polysorbate 20 or polysorbate 80.

In addition, the present invention provides a method of treating atopic dermatitis comprising administering a gel composition to a subject, comprising taurodeoxycholic acid, its derivative, or a pharmaceutically acceptable salt thereof as an active ingredient;

hyaluronic acid, its derivatives or pharmaceutically acceptable salts thereof; and a surfactant that is polysorbate 20 or polysorbate 80.

The above mentioned taurodeoxycholic acid, its derivative thereof or a pharmaceutically acceptable salt thereof, hyaluronic acid, its derivative or a pharmaceutically acceptable salt thereof, a surfactant that is polysorbate 20 or polysorbate 80, and atopic dermatitis are utilized for specific description, consistent with the description of the gel composition, and so the specific description adopts the aforementioned content.

Meanwhile, the gel composition prepared by the method of the present invention exhibits fewer side effects and higher therapeutic effect compared to existing atopic dermatitis treatments, and also has a significantly superior effect compared to the conventional formulation. Therefore, the gel composition of the present invention can be effectively utilized for the prevention, improvement, or treatment of atopic dermatitis.

Hereinafter, the present invention will be described in detail through examples, comparative examples, and experimental examples.

However, the following examples, comparative examples, and experimental examples only illustrate the present invention, and the content of the present invention is not limited to the following examples, comparative examples, and experimental examples.

Example 1. Preparation of Samples

As a composition for preventing or treating atopic dermatitis, 0.5% HY209 gel containing sodium taurodeoxycholate (TDCA) was prepared with the composition shown in Table 1 below.

Sodium taurodeoxycholic acid powder was dissolved by mixing with 20 ml of purified water and polysorbate 80, and then methyl paraoxybenzoate and 70 ml of distilled water were mixed with the 25% sodium taurodeoxycholate solution, sodium hyaluronate was added to the mixed solution, and then purified water was added to make the mixture volume 1000 ml.

TABLE 1

| Constituents | Content (mg) |
|---|---|
| sodium taurodeoxycholate | 5.0 |
| Polysorbate 80 | 0.5 |
| Sodium hyaluronate | 10.0 |
| methyl paraoxybenzoate | 2.0 |
| Purified water | balance |
| Total | 1000 |

<Comparative Example 1> Preparation of 5% HY209_PEG Gel with Different Excipients The sodium taurodeoxycholic acid powder of <Example 1> was dissolved in a 7:3 mixture of polyethylene glycol 400 solution (10% in distilled water) and ethanol stock solution to make 5%, and then filtered through a 0.4 μm filter to produce the formulation.

<Example 2> Production of Atopic Dermatitis-Induced Animal Model by DNCB 200 ml of a solution of 2,4-Dinitrochlorobenzene (DNCB) dissolved in acetone at a concentration of 1% or 2% was applied to the backs of mice with hair removed twice a day for 2 days, then on the 3rd day, a solution of 200 ml containing 1% concentration of DNCB dissolved in acetone was applied twice daily, and additional applications of a solution of 200 mL containing 1% concentration of DNCB dissolved in acetone or a solution diluted 10 times were applied twice daily on the shaved backs of mice until the 10th to 11th day starting from the day of the initial application of DNCB solution, to induce atopic dermatitis (FIG. 1).

<Experimental Example 1> Comparative Confirmation of the Atopic Dermatitis Treatment Effect of 0.5% HY209_HA Gel (Gel) and Our Existing Product, 5% HY209_PEG Gel (Gel), in an Animal Model Through Appearance Observation and Sensory Evaluation For comparative evaluation of the therapeutic effects of 0.5% HY209_HA gel and 5% HY209_PEG gel on atopic dermatitis in the atopic dermatitis-induced animal model of <Example 2> through appearance observation and sensory evaluation, mice with induced atopic dermatitis from <Example 2> were randomly assigned into groups: DNCB group, 0.5% HY209_HA gel group, 5% HY209_PEG gel group, Dexamethasone (DEX) (Maxidex ointment, Alcon Pharmaceutical) group, Crisaborole (Eucrisa ointment, Pfizer Inc.) group, Tofacitinib group, and FK506 (Tacrolimus) (Protopic ointment, Leopharma) group, each consisting of 5 mice.

Each group of mice underwent appearance observation and sensory evaluation of the appearance of atopic dermatitis-induced lesions on their backs. Sensory evaluation involved scoring based on the severity of scratching frequency, erythema and bleeding, edema, excoriation and lichenification, and scaling and dryness, with scores ranging from 0 to 3 for a total score of 15 points on the 15th day after the initiation of DNCB application. Scores were averaged across three blinded evaluators for each mouse individual.

As a result, it was observed that the sensory evaluation index for atopic dermatitis significantly decreased in the 0.5% HY209_HA gel group and the 5% HY209_PEG gel group compared to the DNCB group. Particularly noteworthy was the significant improvement in symptoms of atopic dermatitis in the 0.5% HY209_HA gel group compared to the positive control groups: Dexamethasone (DEX) group, Crisaborole group, Tofacitinib group, and FK506 group, and furthermore, even when compared to the our existing product, the 5% HY209_PEG gel group, it was confirmed that the 0.5% HY209_HA gel group exhibited equivalent or superior therapeutic effects despite a tenfold reduction in HY209 dosage (FIGS. 2 and 3).

<Experimental Example 2> Comparative Confirmation of Atopic Dermatitis Treatment Effect Between 0.5% HY209_HA Gel (Gel) and Our Existing Product, 5% HY209_PEG Gel (Gel), in Animal Model Through Serum Analysis For comparative evaluation of the atopic dermatitis treatment effect through serum analysis of 0.5% HY209_HA gel and 5% HY209_PEG gel in the atopic dermatitis-induced animal model of <Example 2>, each group of individuals who completed the evaluation of <Experimental Example 1> were injected with an anesthetic prepared by mixing 250 mg/5 cc of Zoletil and 2% Rompun solution in at a ratio of 8:2 (v/v), and diluted tenfold with saline solution prior to administration, followed by blood collection from the heart. Next, serum analysis was performed using the usual method.

As a result, it was confirmed that the concentration of cytokines in the serum of the 0.5% HY209_HA gel group and the 5% HY209_PEG gel group improved atopic dermatitis compared to the cytokine concentration in the serum of the DEX group and FK506 group (FIG. 4).

<Experimental Example 3> Comparative Confirmation of the Atopic Dermatitis Treatment Effect of 0.5% HY209_HA Gel (Gel) and Our Existing Product, 5% HY209_PEG Gel (Gel), in an Animal Model by Measuring the Thickness of the Epidermis and Dermis To compare and confirm the therapeutic effects of 0.5% HY209_HA gel and 5% HY209_PEG gel on atopic dermatitis through measurement of the thickness of the epidermis and dermis in the atopic dermatitis-induced animal model of <Example 2>, each individual in the groups treated with 0.5% HY209_HA Gel, 5% HY209_PEG gel, Maxidex ointment, Eucrisa ointment, and Protopic ointment in <Experimental Example 1> had their atopic dermatitis-induced areas scarified on the 15th day from the induction of atopic dermatitis, and the Sham (untreated) group, where atopic dermatitis was not induced, and the DNCB group, which was not treated after the induction of atopic dermatitis, were also scarified on the 15th day.

After collecting skin tissues from each group of mice, the tissue samples were sliced and then fixed in 10% formalin solution for 24 hours, then rinsed with distilled water, processed into paraffin blocks, and sectioned into 7 Mm thickness slices, these slices were stained with Hematoxylin and Eosin (H&E), and observed under an optical microscope, and then the thickness of the epithelium and dermis were measured using image analysis software and analyzed using analysis software.

As a result, an increase in epidermal and dermal thickness was observed in the DNCB group compared to the Sham group, and in contrast, it was confirmed that the skin epithelium thickness was significantly reduced, and the dermal thickness was recovered close to that of the normal Sham group, for the 0.5% HY209_HA gel group, 5% HY209_PEG gel group, DEX group and Crisaborole group and FK506 group compared to the DNCB group. In addition, when comparing the 0.5% HY209_HA gel group with the 5% HY209_PEG gel group, which is our existing product, it was confirmed that the same or greater recovery effect was achieved even though the dose of HY209 was reduced by 10 times (FIGS. 5 to 7).

<Experimental Example 4> Comparative Confirmation of Atopic Dermatitis Treatment Effect Between 0.5% HY209_HA Gel and Our Existing Product, 5% HY209_PEG Gel, in an Animal Model by Measuring Spleen Weight To compare and confirm the atopic dermatitis treatment effect of 0.5% HY209_HA gel and 5% HY209_PEG gel through spleen weight measurement in the atopic dermatitis-induced animal model of <Example 2>, each individual from the groups treated with 0.5% HY209_HA gel, 5% HY209_PEG gel, Maxidex ointment, Eucrisa ointment, Tofacitinib and Protopic ointment in <Experimental Example 1> was sacrificed on the 15th day from the induction of atopic dermatitis, and additionally, the Sham (untreated) group, where atopic dermatitis was not induced, and the DNCB group, which was not treated after the induction of atopic dermatitis, were also sacrificed on the $15^{th}$ day.

Tissue samples from the spleen were collected from the sacrificed mice in each group, and the weight of the collected spleen samples was measured.

As a result, it was observed that the weight of the spleen, which had enlarged due to DNCB, was similar to that of Sham group in the group treated with HY_HA gel, indicating a recovery of general health and immune status close to normal in mice treated with this gel, and furthermore, when compared to our existing product, the 5% HY209_PEG gel group, it was confirmed that despite a tenfold reduction in HY209 dosage, the 0.5% HY209_HA gel exhibited equivalent or superior therapeutic effects (FIG. 8).

<Example 3> Production of Atopic Dermatitis-Induced Animal Model by MC903

A 1 nM solution of Calcipotriol (MC903) was applied to the back of hair-removed mice twice a day for 9 days to induce atopic dermatitis (FIG. 9).

<Experimental Example 5> Confirmation of Atopic Dermatitis Treatment Effect of 0.5% HY209_HA Gel in Animal Model Through Appearance Observation and Sensory Evaluation To confirm the therapeutic effects of 0.5% HY209_HA gel on atopic dermatitis through appearance observation and sensory evaluation in the atopic dermatitis-induced animal model of <Example 3>, mice induced with atopic dermatitis from <Example 3> were randomly assigned into groups: MC903 group and the 0.5% HY209_HA gel group, each consisting of 5 mice, based on the treatment method.

The appearance and sensory evaluation of the induced atopic dermatitis on the backs of mice in each group were conducted to assess the improvement of atopic dermatitis, and the sensory evaluation included scoring based on the severity of scratching frequency, erythema and bleeding, edema, excoriation and lichenification, and scaling and dryness, with scores ranging from 0 to 3 for a total score of 15 points for 2 minutes on the 10th day after the initiation of MC903 solution application. Scores were averaged across three blinded evaluators for each mouse individual.

As a result, the 0.5% HY209_HA gel group had a significantly reduced sensory evaluation index for atopic dermatitis compared to the MC903 group, and the results of measuring the thickness of the ear also confirmed that it had a therapeutic effect on atopic dermatitis symptoms (FIG. 10).

<Experimental Example 6> Confirmation of the Atopic Dermatitis Treatment Effect of 0.5% HY209_HA Gel in an Animal Model by Measuring the Thickness of the Epidermis and Dermis To confirm the therapeutic effects of 0.5% HY209_HA gel on atopic dermatitis through measurement of the thickness of the epidermis and dermis in the atopic dermatitis-induced animal model of <Example 3>, each individual in the groups treated with 0.5% HY209_HA gel in <Experimental Example 5> had their atopic dermatitis-induced areas scarified on the 10th day from the induction of atopic dermatitis, and the Sham (untreated) group, where atopic dermatitis was not induced, and the MC903 group, which was not treated after the induction of atopic dermatitis, were also scarified on the 10th day.

After collecting skin tissues from each group of mice, the tissue samples were sliced and then fixed in 10% formalin solution for 24 hours, then rinsed with distilled water, processed into paraffin blocks, and sectioned into 7 Mm thickness slices, these slices were stained with Hematoxylin and Eosin (H&E), and observed under an optical microscope, and then the thickness of the epithelium and dermis were measured using image analysis software and analyzed using analysis software.

As a result, an increase in epidermal and dermal thickness was observed in the MC903 group compared to the Sham group, and in contrast, in the 0.5% HY209_HA gel group, the skin epithelium thickness was significantly reduced compared to the MC903 group, and it was confirmed that there was a close recovery to the Sham group with normal dermal thickness (FIG. 11).

<Example 4> Production of Atopic Dermatitis-Induced Animal Model by Oxazolone After applying a 1% oxazolone solution once to the back of a mouse after hair removal, 0.1% oxazolone was additionally applied twice a day on the 8th, 10th, and 15th days to induce atopic dermatitis (FIG. 12).

<Experimental Example 7> Confirmation of Atopic Dermatitis Treatment Effect of 0.5% HY209_HA Gel in Animal Model Through Appearance Observation and Sensory Evaluation To confirm the therapeutic effect of 0.5% HY209_HA gel on atopic dermatitis through appearance observation and sensory evaluation in the atopic dermatitis-induced animal model of <Example 4>, mice induced with atopic dermatitis from <Example 4> were randomly assigned into groups: Oxazolone group and 0.5% HY209_HA gel group, each consisting of 5 mice, based on the treatment method.

The appearance and sensory evaluation of the induced atopic dermatitis on the backs of mice in each group were conducted to assess the improvement of atopic dermatitis, and the sensory evaluation included scoring based on the severity of scratching frequency, erythema and bleeding, edema, excoriation and lichenification, and scaling and dryness, with scores ranging from 0 to 3 for a total score of 15 points for 2 minutes on the 10th day after the initiation of oxazolone solution application. Scores were averaged across three blinded evaluators for each mouse individual.

As a result, the 0.5% HY209_HA group a gel had significantly reduced sensory evaluation index for atopic dermatitis compared to the oxazolone group, and the results of measuring the thickness of the ear also confirmed that it had a therapeutic effect on atopic dermatitis symptoms (FIG. 13).

<Experimental Example 8> Confirmation of the Atopic Dermatitis Treatment Effect of 0.5% HY209_HA Gel in an Animal Model by Measuring the Thickness of the Epidermis and Dermis To confirm the therapeutic effects of 0.5% HY209_HA gel on atopic dermatitis through measurement of the thickness of the epidermis and dermis in the atopic dermatitis-induced animal model of <Example 4>, each individual in the groups treated with 0.5% HY209_HA gel in <Experimental Example 7> had their atopic dermatitis-induced areas scarified on the 17th day from the induction of atopic dermatitis, and the Sham (untreated) group, where atopic dermatitis was not induced, and the oxazolone group, which was not treated after the induction of atopic dermatitis, were also scarified on the 17th day.

After collecting skin tissues from each group of mice, the tissue samples were sliced and then fixed in 10% formalin solution for 24 hours, then rinsed with distilled water, processed into paraffin blocks, and sectioned into 7 Mm thickness slices, these slices were stained with Hematoxylin and Eosin (H&E), and observed under an optical microscope, and then the thickness of the epithelium and dermis were measured using image analysis software and analyzed using analysis software.

As a result, an increase in epidermal and dermal thickness was observed in the oxazolone group compared to the Sham group, and in contrast, in the 0.5% HY209_HA gel group, the skin epithelium thickness was significantly reduced compared to the oxazolone group, and it was confirmed that there was a close recovery to the Sham group with normal dermal thickness (FIG. 14).

INDUSTRIAL APPLICABILITY

The present invention relates to a gel composition comprising a taurodeoxycholic acid, its derivative, or a pharmaceutically acceptable salt thereof as an active ingredient, and hyaluronic acid, its derivative, or a pharmaceutically acceptable salt thereof; and a surfactant such as polysorbate 20 or polysorbate 80, and a composition comprising the same for preventing or treating atopic dermatitis, specifically, the composition demonstrates reduced side effects and enhanced therapeutic efficacy compared to existing treatments for atopic dermatitis, it has the advantage of having a significantly superior effect compared to conventional formulations, and so it can be usefully used.

What is claimed is:

1. A gel composition comprising taurodeoxycholic acid or a pharmaceutically acceptable salt thereof as an active ingredient;

hyaluronic acid or a pharmaceutically acceptable salt thereof; and polysorbate 80.

2. The gel composition of claim 1, wherein the taurodeoxycholic acid or the pharmaceutically acceptable salt thereof is sodium taurodeoxycholic acid.

3. The gel composition of claim 1, wherein the taurodeoxycholic acid or the pharmaceutically acceptable salt thereof is included in an amount of 0.01 to 3 w/v % based on the entire gel composition.

4. The gel composition of claim 1, wherein the taurodeoxycholic acid or the pharmaceutically acceptable salt thereof is included in an amount of 0.02 to 0.5 w/v % based on the entire gel composition.

5. The gel composition of claim 1, wherein the taurodeoxycholic acid or the pharmaceutically acceptable salt thereof is included in an amount of 0.05 to 0.1 w/v % based on the entire gel composition.

6. The gel composition of claim 1, wherein the hyaluronic acid or the pharmaceutically acceptable salt thereof is sodium hyaluronic acid.

7. The gel composition of claim 1, wherein the hyaluronic acid or the pharmaceutically acceptable salt thereof is included in an amount of 0.1 to 2 w/v % based on the entire gel composition.

8. The gel composition of claim 1, wherein the hyaluronic acid or the pharmaceutically acceptable salt thereof is included in an amount of 0.5 to 1.5 w/v % based on the entire gel composition.

9. The gel composition of claim 1, wherein the hyaluronic acid or the pharmaceutically acceptable salt thereof is included at 1 w/v % based on the entire gel composition.

10. The gel composition of claim 1, wherein the polysorbate 80 is included in an amount of 0.01 to 1 w/v % based on the entire gel composition.

11. The gel composition of claim 1, wherein the polysorbate 80 is included in an amount of 0.02 to 0.5 w/v % based on the entire gel composition.

12. The gel composition of claim 1, wherein the polysorbate 80 is included in an amount of 0.03 to 0.1 w/v % based on the entire gel composition.

13. The gel composition of claim 1, wherein the polysorbate 80 is included at 0.05 w/v % based on the entire gel composition.

14. The gel composition of claim 1, wherein further comprising a preservative.

15. The gel composition of claim 14, wherein the preservative is methyl paraoxybenzoate.

16. The gel composition of claim 14, wherein the preservative is included in an amount of 0.05 to 1 w/v % based on the entire gel composition.

17. The gel composition of claim 14, wherein the preservative is included in an amount of 0.1 to 0.5 w/v % based on the entire gel composition.

18. The gel composition of claim 14, wherein the preservative is included at 0.2 w/v % based on the entire gel composition.

19. A method for improving atopic dermatitis, comprising the step of administering a gel composition to a subject, said gel composition comprising taurodeoxycholic acid or a pharmaceutically acceptable salt thereof as an active ingredient;

hyaluronic acid or a pharmaceutically acceptable salt thereof; and polysorbate 80.

20. A method for treating atopic dermatitis, comprising the step of administering a gel composition to a subject, said gel composition comprising taurodeoxycholic acid or a pharmaceutically acceptable salt thereof as an active ingredient;

hyaluronic acid or a pharmaceutically acceptable salt thereof; and polysorbate 80.

* * * * *